(12) United States Patent
Komatsuda et al.

(10) Patent No.: US 7,518,040 B2
(45) Date of Patent: Apr. 14, 2009

(54) METHODS OF IDENTIFYING SPIKE MORPHOLOGY AND FUSARIUM HEAD BLIGHT RESISTANCE, AND THE USE OF THESE METHODS FOR IMPROVING BARLEY AND RELATED TRITICEAE PLANTS

(75) Inventors: Takao Komatsuda, Ibaraki (JP); Badraldin Ebrahim Sayed-Tabatabaei, Ibaraki (JP); Congfen He, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 254 days.

(21) Appl. No.: 10/553,723

(22) PCT Filed: Apr. 15, 2004

(86) PCT No.: PCT/JP2004/005407

§ 371 (c)(1),
(2), (4) Date: Feb. 23, 2006

(87) PCT Pub. No.: WO2004/092366

PCT Pub. Date: Oct. 28, 2004

(65) Prior Publication Data

US 2006/0236422 A1    Oct. 19, 2006

(30) Foreign Application Priority Data

Apr. 15, 2003 (JP) .............................. 2003-110682

(51) Int. Cl.
*A01H 5/00* (2006.01)
*C12Q 1/68* (2006.01)

(52) U.S. Cl. ............................. 800/320; 800/298; 435/6
(58) Field of Classification Search ....................... None
See application file for complete search history.

(56) References Cited

FOREIGN PATENT DOCUMENTS

WO    WO 2004/092366 A1    10/2004

OTHER PUBLICATIONS

Mesfin et al. Crop Science (2003), vol. 43, pp. 307-318.*
Tanno et al. Theor Appl Genet (2002) 104:54-60.*
Jui et al. Theor. Appl Genet (1997) 94:549-656.*

Ayoub et al., "QTLs affecting kernel size and shape in a two-rowed barley cross," Theor. Appl. Genet., 2002, pp. 237-247, vol. 105.
De La Pena et al, "Quantitative trait loci associated with resistance to Fusarium head blight and kernel discoloration in barley," Theor. Appl. Genet., 1999, pp. 561-569, vol. 99.
Fernandez et al., "The use of ISSR and RAPD markers for detecting DNA polymorphism, genotype identification and genetic diversity among barley cultivars with known origin," Theor. Appl. Genet., 2002, pp. 845-851, vol. 42.
He et al., "AFLP targeting of the 1-cM region conferring the vrs1 gene for six-rowed spike in barley, *Hordeum vulgare* L.," Genome, Dec. 2004, pp. 1122-1129, vol. 44, No. 6.
Komatsuda et al., "Comparative high resolution map of the six-rowed spike locus 1 (vrs1) in several populations of barley, *Hordeum vulgare* L.," Hereditas, 2004, pp. 68-73, vol. 141.
Mano et al., "Map construction of sequence-tagged sites (STSs) in barley (*Hordeum vulgare* L.)," Theor. Appl. Genet., 1999. pp. 937-946, vol. 98.
Mesfin et al., "Quantitative trait loci for Fusarium head blight resistence in barley detected in a two-rowed by six-rowed population," Crop. Sci., Jan.-Feb. 2003, p. 307-318, vol. 43.
Saito et al., "Shin Kaihatsu no Seigen Koso Danpencho Tagata (RFLP) Marker o Fukumu Omugi RFLP Chizu," Seibutsu Shigen Kenkyu Seika Joho, 1999, pp. 61-62, No. 8.
Tanno et al., "A DNA marker closely linked to the vrs1 locus (row-type gene) indicates multiple origins of six-rowed cultivated barley (*Hordeum vulgare* L.)," Theor. Appl. Genet., 2002, pp. 54-60, vol. 104.
Urrea et al., "Heritability of Fusarium head blight resistence and deoxynivalenol accumulation from barley accession C Iho 4196," Crop. Sci., 2002, pp. 1404-1408, vol. 24.
Zhu et al., "Does function follow form? Principal QTLs for Fusarium head blight (FHB) resistance are coincident with QTLs for inflorescence traits and plant height in a double-haploid population of barley," Theor. Appl. Genet., 1999, pp. 1221-1232, vol. 99.
PCT International Search Report, PCT/JP2004/005407, dated May 25, 2004.
PCT International Preliminary Examination Report, PCT/JP2004/005407, dated Apr. 26, 2005, 8 pages.

* cited by examiner

*Primary Examiner*—Medina A Ibrahim
(74) *Attorney, Agent, or Firm*—TraskBritt

(57) ABSTRACT

Using crossbred segregating populations of two-rowed and six-rowed barley cultivars, the row type of individual plants was precisely determined. The results indicate that row type is controlled by a single gene. In addition, it was discovered that molecular markers linked with this gene could be used to identify whether a test barley or related *Triticeae* plant is two-rowed or six-rowed. Furthermore, molecular markers can be used to identify Fusarium head blight resistance, which is linked with the two-rowed or six-rowed gene.

9 Claims, 4 Drawing Sheets

```
AFLP1(SEQ ID NO: 1)
GACTGCGTACCAATTCGCTGAGGTACTTGCTCGCATAGTCATGGTGCTCTTTGCAAACTGCCAA
GAAGCTCTCGTGCATATAGTATGGGTCCGCGATGCAGATATATTTGATGCTCTCCGTCCTGATG
AAGTAGTTGAGATACAGCGCATACATGCGGATGAACTGGAAATCCAACTTGGTCATGTGGAACA
TATTGTAGATGTAGTCAAATCGCAGGAGGAATTGATTCGCGGGCCAGGTATCGAAGTACACCTT
CCCACCCGGCACCTGAGCCGCGTAAAGCGGGTATCCTGAATCTTTCACGACCAGAAGGCTTTTC
TCTCTGGCCAGCACATCTTCATGGAGTCTCTTTAGATCATTGTTCAGTACGTGATCTATTGTTT
TGGCAGGTAGGATCGGCTTGCCGGCGACATGGAAATGCTTCTTACCTTCGACGGGTATTCTGTC
TACCACCCGGGGTTCCAGAGGCGGCTAGCTGCTTGAAGCATCTATGGCGCCTTTAAGGGCCTTT
CCTGGCCAGTCTCTTCCTTTGCTTCTTGGTGGGTGGCGGTAGTGAACCCACCATACCTTCCCTA
ACCAGCACCCCAGTGTCATCGGGCTAGACAGTGGACGGCCTCGGGGGGTTGCTGGCTAGAGGT
GGCATCTCGAGGCGTCTCCTGCGAGGATGGCTTGAAGAGAGACTTTTTGCATTCCACCTTAGGA
CGTTCCGGCTCCGGAAAATCAGGCAACATCAAGTCATCGTCTCCACACTCATAGCCTATTTCTT
CGGCGTCATGAGCCATCAATCCATCATAGGCGGTATTGAAATACTTGTTCGGGTCCTCATCATC
ATCCTCCATGTCATTATCAACATTTGCTTCTTCGACAGTGGGGTGACATGATCTGGCACTAATG
GAGGCTCTCCCTCGCGTTGTACGCTACCATCATCTGCCACGACAGGTGCAAGTAATTTGGTAGG
TGGGATGGTGTTCATACCTTCTTGAGAAGGTGGCGTTGGAGTGATACTGGGCTCCTCGAGACGA
ATAAGAGACTTCGGCCAAGGCAAGAATCAGTTCTTGCATGCGCCAATCATCTTACTCAGGACTC
ATC

AFLP2(SEQ ID NO: 2)
GACTGCGTACCAATTCGACTAGCCATGGTTGTGTATGTATGGCACATGGGAGTAAAACGTTACA
ATTCTTTTTGGGAACCACACATAATGAGTATAGCATGGAAGATACTAATAACGTTTGTCGTAAC
GTTCACAGTAAAGAACACCACTCAAAATTATATTTTCAATCCCGCTTTGAAAACTTGAGCTCTA
GGACTTGTGCAAATCAATGCTTACCTCTGCAAAGGGTCTATCTATTTACTCAGGACTCATC
```

FIG. 3

AFLP3 (SEQ ID NO: 3)
GACTGCGTACCAATTCTATTAGTGACAATCATGCTAAAAATATGCAAAACCCTAAGCTTGGGGA
TGCTAGTTTTGCTATGACCACTACATGATTGGGGTAATAATTTTTCTTATTGTGACATCCCCGG
ATTTAGGCTACAGTAATCTTGGTAATTGAACTACAGTAAACATATGCAAAGGATGCCACATCAT
CGTGATTCTATTATTGATCTCGTGATAGTCGAAACCGAGTCGAAAATCGAAGTTACTCAGGACT
CATC

AFLP4 (SEQ ID NO: 4)
GACTGCGTACCAATTCCTGTGTGGGAAGGGGAAAACCAAAGCCATCATCATCACCAACGCTTCC
TCCTTCGTGGGAGGATCGATCTTCATCAACATATTCACCAGCACCATCTCATGTCCAACCCTAG
TTCATCTCGTGTATTTACTCAGGACTCATC

AFLP5 (SEQ ID NO: 5)
GACTGCGTACCAATTCCTGCTGGAGAAAGACGAGGTGCTGGAGGTGGTTGTCGGTGAAGAGCAC
GTTCAGCTTCGTCTAGACGGAGTAGGCACCATCATCATCATGAACCACCGTGTCGAAGAGATCC
TTCGAGATGGTGTGGAAGAATGTCACGCCCAAGATGCGACCCTATCCTCAATTTGGCACGAAGG
CCTTGTCATGGATAGAAGCGCATCTCGTCGTGTCGCAAGAATGGATATCGTTACAAGTACATGT
ACTGAAAAGAAGAGATATATATAGAATTGGCTTACACTCGCCACAAGCTACATCAGAGTCACAT
CAGTACATTACATAATCATCAAGAGCAAGAGCAGGGTCCGACTACGGACGAAAACAAACGATAA
AAATAAGAACAGCGTCCGTCCTTGCTATCCCAGGCTGCCGGCCTGGAACCCATCCTAGATCGAT
GAAGAAGAAGAAGAAGCAACTCCAAATGAACAATCAAGGCGCTCGCGTTACTCAGGACTCA
TC

FIG. 4

METHODS OF IDENTIFYING SPIKE MORPHOLOGY AND FUSARIUM HEAD BLIGHT RESISTANCE, AND THE USE OF THESE METHODS FOR IMPROVING BARLEY AND RELATED TRITICEAE PLANTS

CROSS-REFERENCE TO RELATED APPLICATIONS

This is a national phase entry under 35 U.S.C. §§ 371 of International Application No. PCT/JP04/005407, filed Apr. 15, 2004, published in English, which claims the benefit under 35 U.S.C. § 119 of Japanese Patent Application Serial No. 2003-110682 JP, filed Apr. 15, 2003, the contents of each of which are incorporated by this reference.

TECHNICAL FIELD

This invention relates to methods of identifying genes that control spike morphology and resistance to Fusarium head blight in barley and related *Triticeae* plants.

BACKGROUND ART

The world's most important cereal grains—rice, wheat, barley, and corn—are all crops whose seeds (embryo and endosperm) are used as food. In barley, each rachis forms three monanthous spikelets. Those in which all three spikelets bear seeds are called six-rowed barleys; those in which only the center spikelet bears seeds are called two-rowed barleys. Although two-rowed and six-rowed barleys are the same biological species, their origins and history are different, and the plants have many different morphological, physiological, and ecological traits, which contributes to their different qualities and uses. It is believed that six-rowed barley first came to Japan from Eurasia around the first century. Six-rowed barley has been long used as a food to supplement rice, and has also been used as livestock feed. It is also used as an ingredient for making miso and soy sauce. In contrast, two-rowed barley was introduced from Europe during the Meiji era or later. Two-rowed barley is characterized by a low protein content and high starch ratio. It has superior uniformity in the malting process, and is thus mainly used for beer brewing.

Differences in barley row type are known to be controlled by a single gene (vrs1), which is localized on chromosome 2. Detailed comparisons of the morphologies of two-rowed and six-rowed barleys show a number of notable changes in two-rowed barley, such as a size reduction in the two lateral spikelets of the three spikelets, regression of stamens, trailed pistils, and disappearance of aristae, revealing pleiotropic expression of a single gene. In addition, agronomically important traits such as flowering time and plant height, and a variety of brewing characteristics, are linked to the genomic region containing the gene that controls row type. Thus, the genomic region is particularly important. Moreover, it was recently found that the gene for resistance to Fusarium head blight in barley and related *Triticeae* plants (quantitative trait loci: QTL) is closely linked with the gene that controls row type in barley (de la Pena et al. Theor. Appl. Genet. 99: 561-569 (1999); Zhu et al. Theor. Appl. Genet. 99: 1221-1232 (1999)).

Fusarium head blight (FHB) in barley and related *Triticeae* plants is a serious disease that contaminates many *Gramineae* plants crops such as wheat, barley, and oats, not only reducing the commercial values of these grains, but also producing mycotoxins such as deoxynivalenol. Deoxynivalenol is an extremely dangerous toxin, causing gastrointestinal disorders accompanied by hemorrhagic conditions and the like in humans and animals that eat infected grains, leading to death in some cases. Since deoxynivalenol is stable against changes in pH and heat, detoxification is difficult. Therefore, grains contaminated beyond a certain level cannot be used in any form of brewing, processing, or livestock feed, and are thus disposed of. The pathogen *Fusarium* spp. is a very common saprobe, spread across grain cultivating areas all over the world, and known to cause severe damage, particularly in areas with high rainfall between flowering and grain filling. On the other hand, increased concerns about food safety have led to requests for cultivation using as little pesticides as possible. Thus, development of disease-resistant cultivars is essential in improving the safety of barley and related *Triticeae* plants. These problems require urgent solution not only in Asia, but also across the globe, including the United States and Europe.

However, progress in improving barley resistance to Fusarium head blight has been slow. The reasons for this are as follows: The small number of resistant barley cultivars also carry a number of agronomically unfavorable traits, and can not be effectively used as breeding materials. In addition, the resistance trait can only be identified during maturation stages, making it impossible to use a marker to carry out early selection for resistance. Moreover, designing appropriate breeding strategies has been difficult, since it was not clear whether resistance is controlled by the same gene that controls row type, or whether the two genes are closely linked with each other and difficult to separate. Thus, to solve these problems, the development of molecular markers and establishment of identification methods using earlier generations has been desired.

DISCLOSURE OF THE INVENTION

The present invention was made in consideration of the above circumstances. An objective of the present invention is to provide methods for specifically and efficiently identifying two-rowed or six-rowed barleys, as well as methods for specifically and efficiently identifying Fusarium head blight resistance, which is linked to the two-rowed or six-rowed gene.

In order to achieve the above objectives, the present inventors carried out intense studies. Komatsuda et al. had previously constructed detailed linkage maps based on crossbred populations of the six-rowed barley cultivar "Azumamugi" and the two-rowed barley cultivar "Kanto Nakate Gold," and reported that in barley the row type gene is localized to the long arm of chromosome 2H (position shown in the linkage map in FIG. 1) (Komatsuda et al. Genome 42: 248-253 (1999)). The present inventors integrated information on the segregation of row type and molecular markers in individual plants from the linkage maps by Komatsuda et al., and similar information from the linkage maps obtained herein, and constructed detailed linkage maps (FIG. 2).

The inventors made near-isogenic lines in which the two-rowed gene in the two-rowed barley cultivar "Kanto Nakate Gold" was introduced to the six-rowed barley cultivar "Azumamugi" (FIG. 1). The present inventors then combined DNAs obtained from several two-rowed plants and several six-rowed plants respectively in these near-isogenic lines. Then, based on these combined genotypes, molecular markers showing polymorphism in both plant groups were searched by bulk segregation analysis, which is used to find gene polymorphism. In addition, correspondences between DNA markers found in the above lines "Kanto Nakate Gold"

and "Azumamugi" were identified. As a result, the inventors found that the gene controlling row type is localized to the position shown in the linkage map of FIG. 2, and that the gene can be detected using the molecular markers shown in the map. The present inventors thus completed the present invention.

Thus, the present invention relates to methods of specifically and efficiently identifying row type or Fusarium head blight resistance in barley and related *Triticeae* plants, and provides the following (1) to (23):

(1) a method of identifying row type or Fusarium head blight (FHB) resistance in a barley or related *Triticeae* plant, comprising the use of at least one molecular marker shown in the linkage maps of FIGS. 1 and 2, that is linked with a gene that controls row type;

(2) the method of (1), wherein a test plant is identified as having two-rowed or six-rowed spikes when a molecular marker in the test plant shows the same type as a barley or related *Triticeae* plant that is two-rowed or six-rowed, respectively;

(3) the method of (1), wherein the test plant is identified as FHB resistant or FHB susceptible when the molecular marker in the test plant shows the same type as a barley or related *Triticeae* plant that is FHB resistant or FHB susceptible, respectively;

(4) the method of any one of (1) to (3), wherein the molecular marker comprises the nucleotide sequence set forth in any of SEQ ID NOS:1 to 5, or a partial sequence thereof;

(5) the method of any one of (1) to (4), comprising the following steps (a) to (d):
  (a) preparing a DNA sample from a barley or related *Triticeae* plant;
  (b) digesting the prepared DNA sample with a restriction enzyme;
  (c) separating the DNA fragments by size; and
  (d) comparing the size of a detected DNA fragment with that of a control;

(6) the method of any one of (1) to (4), comprising the following steps (a) to (d):
  (a) preparing a DNA sample from a barley or related *Triticeae* plant;
  (b) performing a PCR reaction using primer DNAs, with the prepared DNA sample as a template;
  (c) separating the amplified DNA fragments by size; and
  (d) comparing the size of a detected DNA fragment with that of a control;

(7) The method of any one of (1) to (4), comprising the following steps (a) to (e):
  (a) preparing a DNA sample from a barley or related *Triticeae* plant;
  (b) digesting the prepared DNA sample with a restriction enzyme;
  (c) performing an AFLP reaction using the digested DNA sample as a template;
  (d) separating the amplified DNA fragments by size; and
  (e) comparing the detected DNA pattern with that of a control;

(8) the method of any one of (1) to (7), wherein the barley or related *Triticeae* plant is a barley;

(9) a reagent for identifying row type or FHB resistance in a barley or related *Triticeae* plant, comprising an oligonucleotide of at least 15 nucleotides that is complementary to a DNA comprising the nucleotide sequence set forth in any of SEQ ID NOS:1 to 5, or a complementary strand thereof;

(10) a reagent for identifying row type or FHB resistance in a barley or related *Triticeae* plant, comprising an oligonucleotide comprising the nucleotide sequence set forth in any of SEQ ID NOS:6 and 7;

(11) the reagent of (9) or (10), wherein the barley or related *Triticeae* plant is a barley;

(12) a method of generating an artificially altered barley or related *Triticeae* plant having two-rowed spikes, comprising the step of selecting at an early stage a plant identified as being two-rowed using the method of any one of (1) to (7);

(13) a method of generating an artificially altered barley or related *Triticeae* plant having six-rowed spikes, comprising the step of selecting at an early stage a plant identified as being six-rowed using the method of any one of (1) to (7);

(14) a method of generating an artificially altered barley or related *Triticeae* plant having a trait of FHB resistance, comprising the step of selecting at an early stage a plant identified as FHB resistant using the method of any one of (1) to (7);

(15) a method of generating an artificially altered barley or related *Triticeae* plant having a trait of FHB susceptibility, comprising the step of selecting at an early stage a plant identified as FHB susceptible using the method of any one of (1) to (7);

(16) the method of any one of (12) to (15), wherein the barley or related *Triticeae* plant is barley;

(17) a barley or related *Triticeae* plant having two-rowed spikes, generated by the method of (12);

(18) a barley or related *Triticeae* plant having six-rowed spikes, generated by the method of (13);

(19) a barley or related *Triticeae* plant with FHB resistance, generated by the method of (14);

(20) a barley or related *Triticeae* plant with FHB susceptibility, generated by the method of (15);

(21) the barley or related *Triticeae* plant of any one of (17) to (20), wherein the barley or related *Triticeae* plant is a barley;

(22) a barley or related *Triticeae* plant, which is a progeny or clone of the barley or related *Triticeae* plant of any one of (17) to (21); and

(23) a reproductive material of the barley or related *Triticeae* plant of any one of (17) to (22).

The present invention provides methods of identifying row type or Fusarium head blight (FHB) resistance in barley and related *Triticeae* plants, using at least one molecular marker shown in the linkage maps of FIGS. 1 and 2 and linked with the gene that controls row type.

The identification methods of the invention enable specific and efficient identification of the two-rowed or six-rowed spikes in a test plant, and of FHB resistance, which is linked to the two-rowed or six-rowed gene, by examining the presence or absence of the "gene that controls row type" in the test plant.

The "gene that controls row type" in the present invention is, for example, localized to the long arm of chromosome 2H in barley. In barley, wheat and rye, genes with common ancestors are generally localized to homoeologous chromosomes. Thus, the gene controlling row type in wheat or rye is predicted to be localized to the homoeologous chromosome group 2. The chromosomes corresponding to barley chromosome 2H are 2A, 2B and 2D in wheat, and 2R in rye.

The "gene that controls row type" in the present invention may be called the "six-rowed gene" in six-rowed barleys and related *Triticeae* plants, and the "two-rowed gene" in two-rowed barleys and related *Triticeae* plants.

In the identification methods of the invention, a barley or related *Triticeae* plant of interest (also described as a "test plant") whose row type is to be identified is determined to have the two-rowed spikes if it contains the "two-rowed gene." On the other hand, if the plant contains the "six-rowed gene," it is determined to have the six-rowed spikes.

In a preferred embodiment of the identification methods of the present invention, molecular markers that are linked with the gene that controls row type are used. Herein, a "molecular marker" means a DNA region that is genetically linked with the gene that controls row type and is distinguishable from other DNA regions. Examples of the preferred molecular markers of the present invention are those described in FIGS. 1 and 2.

In general, as the map distance (expressed by the unit cM) between a molecular marker and a gene of interest becomes shorter, the marker and the gene are more closely localized to each other, and more likely to be inherited simultaneously; thus such markers are more useful. Specifically, preferred molecular markers of the invention include AFLP1(e40m36-1110) (SEQ ID NO:1), AFLP2(e34m13-260) (SEQ ID NO:2), AFLP3(e52m32-270) (SEQ ID NO:3), AFLP4 (e31m13-160) (SEQ ID NO:4), AFLP5(e31m26-520) (SEQ ID NO:5), or partial region thereof. AFLP1 to AFLP5 are extremely useful markers since they are localized in close proximity of the "gene that controls row type" (localized to the position denoted as "vrs1" in FIG. 1), and linked with the gene by short map distances within 1 cM.

Information on the molecular markers of the invention shown in FIG. 2, other than AFLP1 to AFLP5, can be obtained from the literature of Komatsuda et al. (Komatsuda et al. Genome 42: 248-253 (1999)) and Mano et al. (Mano Y. et al. Map construction of sequence-tagged sites (STSs) in barley (*Hordeum vulgare* L.). Theor. Appl. Genet. 98: 937-946 (1999)).

For example, in a preferred embodiment of the invention, when segregating populations are made using a six-rowed cultivar carrying the molecular marker of the present invention AFLP2 (e34m13-260), and a two-rowed cultivar without the marker, there is a high probability that plants carrying AFLP2 (e34m13-260), selected by marker analysis, will carry the six-rowed gene.

In addition, when the molecular markers of the invention are used as AFLP markers, if, for example, a test plant (segregant) and its two-rowed parents share the AFLP marker band, the plant has a high probability of being two-rowed.

One embodiment of the invention is methods of identifying two-rowed or six-rowed barleys or related *Triticeae* plants, comprising detecting DNA regions specifically present in a two-rowed or six-rowed barley or related *Triticeae* plant and linked with the gene that controls row type. In these methods the row type of a test plant is usually known, and the lines are in the process of cultivation. In the present methods, if the above-described parents are six-rowed, for example, the test plant is identified as six-rowed when the molecular markers in the test plant are the same types as those of the parent. Molecular markers in test plants and "parents" can be compared not only using DNA sequences, but also using information characteristic of those DNA sequences. Information characteristic of a DNA sequence includes, but is not limited to, the presence or absence of molecular markers, and the presence or absence of mutations and polymorphisms within the molecular markers. Thus, the phrase "are the same type" includes not only cases when the entire DNA sequences of molecular markers are completely identical, but also when information characteristic of the DNA sequences is identical.

Furthermore, in one embodiment of the invention, two or more molecular markers, as shown in FIG. 2, may be appropriately selected to perform the identification methods of the present invention. In this way, more precise identification is possible.

Herein, "using a molecular marker" means utilizing a molecular marker as an index to identify row type or Fusarium head blight (FHB) resistance in barleys or related *Triticeae* plants. Thus, in a preferred embodiment of the invention, a test plant is determined to have six-rowed or two-rowed spikes if molecular markers in the plant are the same type as those of a six-rowed or two-rowed plant, respectively. Furthermore, if the molecular markers of the test plant are the same type as those of FHB resistant or susceptible plants, the test plant is determined to be FHB resistant or susceptible, respectively.

Herein, a "test plant" is not specifically limited, as long as it is a barley or related *Triticeae* plant, including, for example, *Triticeae* plants such as wheat and rye, *Bromeae* plants such as brome grass, *Aveneae* plants such as oats, and *Poeae* plants which include a number of other important grasses. An example of a preferable barley or related *Triticeae* plant in the method of the invention is barley.

Furthermore, for example, six-rowed barley cultivars include "Azumamugi" and "Dissa," and two-rowed barley cultivars include "Kanto Nakate Gold" and "Golden Promise," but they are not limited thereto. The types of molecular markers in any of the above barleys or related *Triticeae* plants, which are already known to be six-rowed or two-rowed or FHB resistant, can be suitably used as a control to perform the identification methods of the invention.

In a preferred embodiment of the present invention, a "test plant" also refers to a line or the like in the process of cultivation, whose parents are known for certain. Thus, test plants showing the same type as two-rowed parents are determined to have a high probability of being two-rowed (containing the two-rowed gene). In this case, the probability can be expressed as 1-0.01×P, in which P(%) is the recombination value.

Molecular markers of the invention include, for example, RFLP (Restriction fragment length polymorphism) markers, RAPD (Random Amplified Polymorphic DNA) markers, AFLP (Amplified Fragment Length Polymorphism) markers, and the like. RFLP markers refer to DNA regions that can be used to determine the presence or absence of RFLPs in chromosomal DNA sequences. RFLPs refer to genetic mutations (such as substitution, insertion, and deletion) that can be detected using differences in the length of DNA fragments obtained by treatment with restriction enzymes. Such mutations can be confined by using agarose gel electrophoresis to separate DNA fragments based on fragment length, and detecting the difference in electrophoresis mobility using Southern blotting.

RAPD methods generally refer to methods of detecting DNA polymorphisms using differences in the length of DNAs amplified using appropriate primers. AFLP methods are essentially a combination of the above RFLP and RAPD methods, and refer to methods of selectively amplifying DNA restriction fragments using PCR to detect differences in their length, or their presence or absence.

The above markers used in the present invention are not particularly limited as long as they are linked with a gene of the invention, and any marker may be used.

When RFLP markers are used as molecular markers of this invention, the identification methods of the present invention may be performed, for example, as below. First, DNA samples are prepared from a barley or related *Triticeae* plant. Next, the prepared DNA sample is digested with restriction enzymes, the DNA fragments are separated based on their size, and the size of the detected DNA fragments is compared with a control. In the above method, if the separation pattern of separated test plant DNAs is the same type as the pattern of a two-rowed or six-rowed or FHB resistant barley or related *Triticeae* plant, the plant is identified as being two-rowed or six-rowed or FHB resistant, respectively.

Specifically, the identification methods of this invention may be carried out as described below, however, they are not limited thereto. First, genomic DNAs are extracted from crossbred progenies (normally green leaves), and treated with the restriction enzyme HindIII. Then, electrophoresis is used to separate digested fragments based on their size, and this is transferred to a nylon membrane, which is subjected to Southern blotting analysis using a probe DNA. The molecular markers of the present invention or partial sequences thereof may be used as such probe DNAs. If the obtained band distribution pattern is the same type as those of a two-rowed or six-rowed or FHB resistant barley or related *Triticeae* plant, the test plant is identified as being two-rowed or six-rowed or FHB resistant, respectively.

The above probe DNAs used in the invention normally hybridize with DNA bands that give rise to the differences corresponding to polymorphisms in the molecular markers of the invention. Specifically, they include each of the molecular markers of the invention or partial sequences thereof.

The probe DNAs may be labeled appropriately, as necessary. Labeling methods include labeling by phosphorylation of the 5'-end of a probe DNA with $^{32}$P using T4 polynucleotide kinase. Alternatively, a probe DNA may be labeled by incorporating nucleotide substrates labeled with isotopes such as $^{32}$P, fluorescent dyes, biotin, or the like using DNA polymerases such as Klenow enzyme with primers such as random hexamer oligonucleotides (random primer method, or the like).

The above hybridization may be carried out under standard hybridization conditions, and preferably under stringent hybridization conditions (for example, conditions described in Sambrook et al., Molecular Cloning, Cold Spring Harbor Laboratory Press, New York, U.S.A., second edition (1989)).

When an RAPD marker is used as a molecular marker of the invention, the identification methods of the present invention may be performed, for example, as follows: First, a DNA sample is prepared from a barley or related *Triticeae* plant. Next, a PCR reaction is performed with primer DNAs, using the prepared DNA sample as a template. Amplified DNAs may be digested with restriction enzymes, as necessary. Then, the amplified DNA fragments are separated by electrophoresis, and the band pattern is compared with that of a barley or related *Triticeae* plant that is two-rowed or six-rowed or FHB resistant. If the band patterns are the same type, the plant is identified as being two-rowed or six-rowed or FHB resistant, respectively.

Optimal primer DNAs for use in the identification methods of the present invention can be appropriately designed by one skilled in the art, taking into account the sequence information of each molecular marker. Normally, the above primers are specific to nucleotide sequences specifically present in barley or related *Triticeae* plants that are two-rowed, or six-rowed, or FHB resistance, and that are linked with the gene that controls row type. Alternatively, the above primers are a set of primer pairs for amplification of a nucleotide sequence that is specifically present in a barley or related *Triticeae* plant which is two-rowed or six-rowed or FHB resistant, and that is linked with the gene controlling row type. The primer pair is designed to flank the nucleotide sequence. The following is a specific example of such a primer set.

```
Primer 1: 5'-ATGGTTGTGTATGTATGGCA-3' (SEQ ID NO:6)
Primer 2: 5'-CAGAGGTAAGCATTGATTTG-3' (SEQ ID NO:7)
```

The PCR primers of the present invention may be prepared by one skilled in the art using, for example, automatic oligonucleotide synthesizers. In addition, one skilled in the art may perform the methods of the present invention using well known methods for polymorphism detection, such as PCR-SSCP using the above PCR primers.

Moreover, if the molecular markers of the invention reside in the exon of a genomic DNA, RT-PCR may be used, using an mRNA as a template. In addition, the Taqman (quantitative PCR detection) system (Roche) may be used to detect the presence or absence of amplified product, using fluorescence. Since this system dispenses with electrophoresis, it is possible to carry out the identification methods of the invention in a short time.

Furthermore, when an AFLP marker is used as a molecular marker of this invention, the identification methods of the invention may be performed as follows: First, a DNA sample is prepared from a barley or related *Triticeae* plant. Next, the DNA sample is treated with a restriction enzyme, and then used as a template for an AFLP reaction. The amplified DNA fragments are then separated by size, and the detected DNA pattern is compared with that of a control. One skilled in the art can easily perform AFLP reactions using optimal restriction enzymes and PCR primers.

An example of the methods of the present invention is described below; however, it is not limited thereto. First, a DNA sample prepared from a test plant is digested with EcoRI and MseI, and then annealed to given AFLP primers and subjected to AFLP reaction to obtain amplified products. The amplified products are analyzed by electrophoresis, and the band pattern is compared with those of two-rowed or six-rowed or FHB resistant plants. If the band patterns are the same type, the test plat is identified as two-rowed or six-rowed or FHB resistant, respectively.

The DNA samples subjected to the identification methods of this invention are not particularly limited, but are normally genomic DNAs extracted from test barleys or related *Triticeae* plants. The source of genomic DNAs is not particularly limited, and any plant tissue can be used for extraction. For example, spikes, leaves, roots, stems, seeds, endosperms, brans, embryos, and such can be used.

In the present invention, the above DNA samples may be prepared (extracted) by methods known to one skilled in the art. An example of a preferred method is the CTAB method for DNA extraction.

Furthermore, the above electrophoresis analysis can be performed according to standard methods. For example, samples may be separated by electrophoresis on an agarose or polyacrylamide gel by applying a voltage, and the pattern of separated DNAs may be analyzed.

Furthermore, the identification methods of the present invention may be performed using more reliable markers, such as CAPS (cleaved amplified polymorphic sequence) and STS (sequence-tagged site) markers derived from the exact sequence analysis of AFLP markers. More specifically, PCR reactions may be carried out using the above primer set (Primers 1 and 2) and DNA from the barley cultivars "Kanto Nakate Gold" and "Azumamugi." When amplified, DNA from each cultivar is treated with DraI, but only the amplified DNA from "Kanto Nakate Gold" is digested by the enzyme, giving rise to a differential mobility upon electrophoresis. Thus, DNAs from the two cultivars can be identified. There are three types of F2 segregating population: homozygotes of both parent's type, and heterozygotes. Since heterozygotes show a combination of both parent's types, the three types can be distinguished.

In addition, the present invention provides reagents for identifying row type or FHB resistance in barleys or related *Triticeae* plants, comprising an oligonucleotide of at least 15 nucleotides that is complementary to a DNA comprising the nucleotide sequence set forth in any of SEQ ID NOS:1 to 5, or a complementary strand thereof.

Herein, "complementary strand" means the other strand in a double stranded nucleic acid, composed of A:T (U, in the case of RNA) and G:C base pairs. In addition, being "complementary" means not only being completely complementary in a region of at least 15 consecutive nucleotides, but also having at least 70%, preferably at least 80%, more preferably 90%, and even more preferably 95% or higher homology to the nucleotide sequence. Any algorithm commonly known to one skilled in the art may be used to determine homology.

The oligonucleotides of the invention hybridize specifically with DNAs comprising the nucleotide sequence set forth in any of SEQ ID NOS:1 to 5, or a complementary strand thereof. Herein, "hybridize specifically" means that the oligonucleotide does not cross-hybridize at a significant level with other DNAs under standard hybridization conditions, and preferably under stringent hybridization conditions (for example, conditions described in Sambrook et al., Molecular Cloning, Cold Spring Harbor Laboratory Press, New York, U.S.A., second edition, (1989)).

The oligonucleotides of the present invention may be used as probes or primers for detecting or amplifying DNAs comprising the nucleotide sequence set forth in any of SEQ ID NOS:1 to 5. In addition, the oligonucleotides may be used as a form of DNA array platform.

When the oligonucleotides are used as primers, they may be normally 15 to 100 bp in length, and preferably 17 to 30 bp. Such primers are not particularly limited, as long as they can amplify at least a part of a DNA of the present invention, or complementary strand thereof. In addition, when used as primers, the oligonucleotides may have a complementary sequence in the 3'-region, and a restriction enzyme recognition site, tag, or the like attached to the 5'-region. The aforementioned primer set (Primers 1 and 2) may be used as a primer set to detect and amplify DNAs comprising the nucleotide sequence shown in SEQ ID NO:2.

When the above oligonucleotides are used as probes, the probes are not particularly limited, as long as they specifically hybridize with at least a part of a DNA comprising the nucleotide sequence set forth in any of SEQ ID NOS:1 to 5, or a complementary strand thereof. Such probes may be synthetic oligonucleotides, normally at least 15 bp in length.

When used as probes, the oligonucleotides of the invention are preferably appropriately labeled. Examples of the labeling methods include phosphorylation of the 5'-end of an oligonucleotide with $^{32}P$ using T4 polynucleotide kinase, and incorporation of a nucleotide substrate labeled with an isotope such as $^{32}P$, a fluorescent dye, biotin, or the like, using a DNA polymerase such as Klenow enzyme with primers such as random hexamer oligonucleotides (random primer methods, or the like).

The oligonucleotides of the invention may be produced using, for example, commercially available oligonucleotide synthesizers. Probes may be prepared as double stranded DNA fragments obtained by treatment with restriction enzymes or such.

As well as including the oligonucleotides as an active ingredient, the reagents for identifying row type or FHB resistance in barleys or related *Triticeae* plants of the present invention may be mixed with, for example, sterile water, physiological saline, plant oils, detergents, lipids, solubilizers, buffers, preservatives, and such, as necessary.

The identification methods of the invention enable selection at an earlier stage of barleys or related *Triticeae* plants that are two-rowed, or six-rowed, or FHB resistant. The present invention also provides methods for selecting, at an earlier stage, barleys or related *Triticeae* plants identified as two-rowed, or six-rowed, or FHB resistant. Herein, an "earlier stage" refers to a stage prior to heading in the barleys or related *Triticeae* plants, and preferably the stage immediately after budding. Furthermore, the present invention provides methods of generating artificially altered barleys or related *Triticeae* plants that have the trait of being two-rowed or six-rowed, or FHB resistant.

Examples of such methods for generating artificially altered barleys or related *Triticeae* plants that have two-rowed or six-rowed spikes include the following (a) to (c), but are not limited thereto:

(a) A two-rowed cultivar is crossed with an arbitrary six-rowed cultivar, and crossbred progenies (hybrids) are repeatedly crossed with the six-rowed cultivar. Then, six-rowed plants are selected from each generation using the methods of the present invention. Alternatively, a six-rowed cultivar is crossed with an arbitrary two-rowed cultivar, and crossbred populations (hybrids) are repeatedly crossed with the two-rowed cultivar. Then, two-rowed plants are selected from each generation using the methods of the present invention.

(b) Row type is altered by introducing the gene that controls row type from a cultivar where the gene is dominant, into a cultivar where the gene is recessive.

(c) Row type is altered by using homologous recombination or such to introduce the gene that controls row type from a cultivar where the gene is recessive, into a cultivar where the gene is dominant.

Examples of methods of generating artificially altered barleys or related *Triticeae* plants carrying FHB resistance include the following (a) to (c), but are not limited thereto.

(a) A FHB resistant cultivar is crossed with an arbitrary FHB susceptible cultivar, and crossbred progenies (hybrids) are repeatedly crossed with the FHB susceptible cultivar. Then, FHB resistant plants are selected from each generation using the identification methods of the present invention.

(b) FHB resistance is altered by introducing the gene that controls FHB resistance from a cultivar where the gene is dominant, to a cultivar where the gene is recessive.

(c) FHB resistance is altered by using homologous recombination or such to introduce the gene that controls FHB resistance from a cultivar where the gene is recessive, to a cultivar where the gene is dominant.

DNA transfection into plants may be performed by methods known to one skilled in the art, such as *Agrobacterium* methods, electroporation, particle gun methods, etc.

In addition, the present invention comprises plants displaying the six-rowed spikes, or two-rowed spikes, or FHB resistance, which are created by the methods of generating artificially altered barleys or related *Triticeae* plants carrying the six-rowed spikes, or two-rowed spikes, or FHB resistant trait.

Once a barley or related *Triticeae* plant with any altered gene is obtained, progenies can be obtained through sexual reproduction or asexual reproduction from the plant. Alternatively, reproductive materials (for example, seed, fruit, cut spike, stem tuber, root tuber, plantlet, callus, protoplast, etc.)

can be obtained from the plant, or progenies or clones thereof, and the plants can be produced on a large scale from these materials.

BRIEF DESCRIPTION OF THE DRAWINGS

FIG. 3 shows an example of the nucleotide sequences of molecular markers AFLP1 and AFLP2 in barley cultivar "Azumamugi." The underlined regions in AFLP2 indicate the nucleotide sequences of PCR primers that can be used in the identification methods of the invention. In barley cultivar "Kanto Nakate Gold," the nucleotide "C" indicated by a double underline is "A," constituting a recognition site for the DraI restriction enzyme.

FIG. 4 shows an example of the nucleotide sequences of molecular markers AFLP3 to AFLP5 in barley cultivar "Azumamugi."

BEST MODE FOR CARRYING OUT THE INVENTION

Herein below, the present invention will be specifically described in detail using examples, however, it is not to be construed as being limited thereto.

EXAMPLE 1

Construction of row type linkage maps and acquisition of molecular markers using BC6F2 and BC7F1 populations of a cross Azumamugi/Kanto Nakate Gold, and F2 populations of Azumamugi/Golden Promise and Azumamugi/Hanna (populations are described in Table 1).

Figure 1:
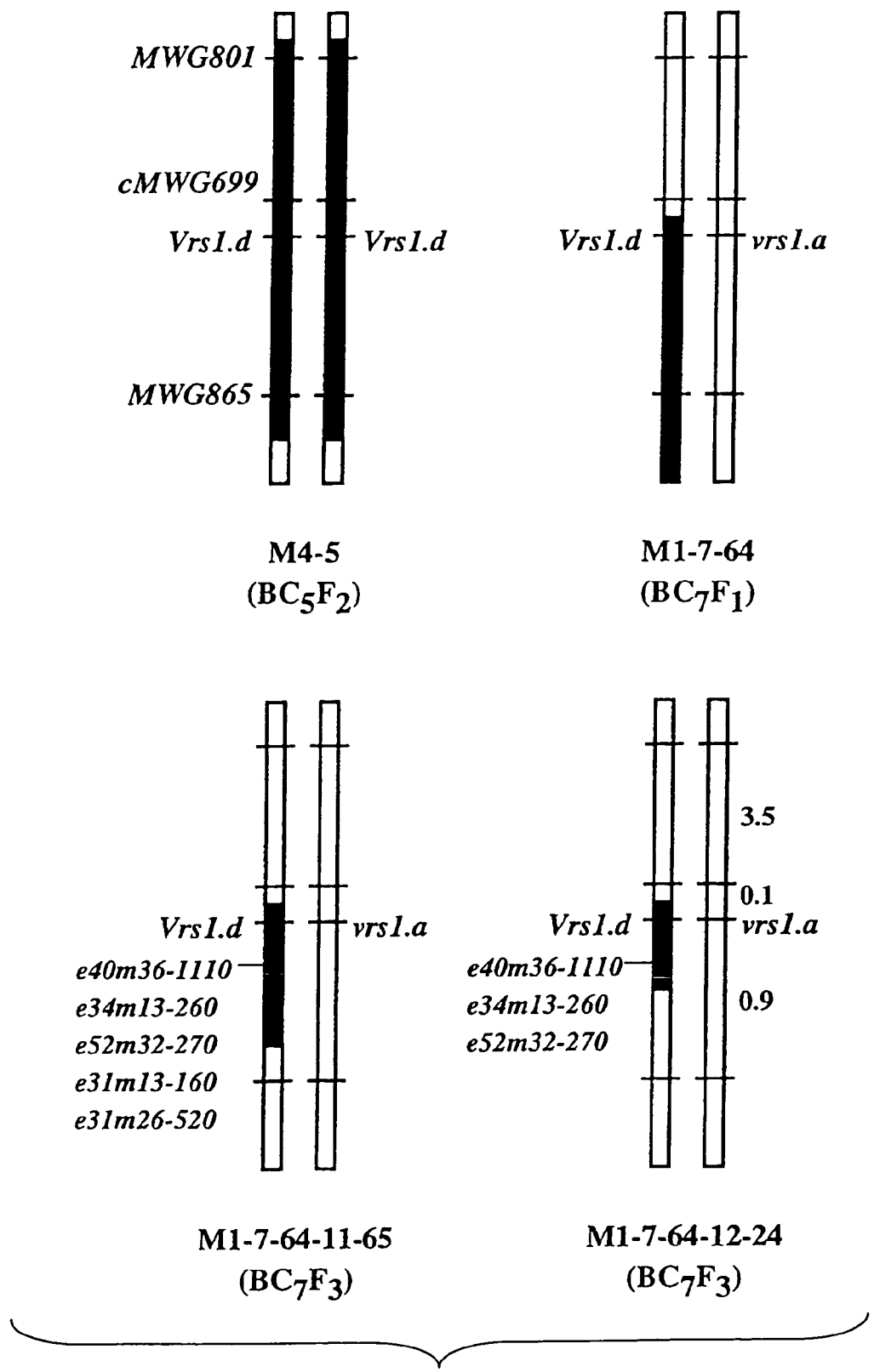
FIG. 1 shows a linkage map showing molecular markers that are linked with the gene that controls row type (vrs1). The five markers beginning with "e" are the AFLP markers generated by the present invention. The other markers were already known. The numbers on the linkage map indicate map distance in cM.

BC7F3, a progeny line of Azumamugi/Kanto Nakate Gold generated by repeated backcrossing (in FIG. 1, M1-7-64-11-65, or M1-7-64-12-24), was further self-fertilized, and eight plants having two-rowed and six-rowed spikes were selected from the progenies. Genomic DNAs were prepared from these materials using SDS methods, and these were digested with EcoRI and MseI, and amplified with non-selective primers. The amplified DNAs from plants of the same row type were combined to obtain bulk DNA.

Next, AFLP methods were performed to amplify the DNAs prepared from the populations of six-rowed and two-rowed plants using a variety of selected primer sets, and polymorphisms were searched to discover five markers that show polymorphisms (Table 2).

TABLE 2

| Code # | AFLP marker | E-000+/M-000+ | Estimated size (bp) | Dominant parental cultivar |
|---|---|---|---|---|
| AFLP1 | e40m36-1110 | GCT/GAT | 1110 | Azumamugi |
| AFLP2 | e34m13-260 | GAC/ATA | 260 | Azumamugi |
| AFLP3 | e52m32-270 | TAT/CTT | 270 | Azumamugi |
| AFLP4 | e31m13-160 | CTG/ATA | 160 | Azumamugi |
| AFLP5 | e31m26-520 | CTG/CGC | 520 | Azumamugi |

Figure 2:
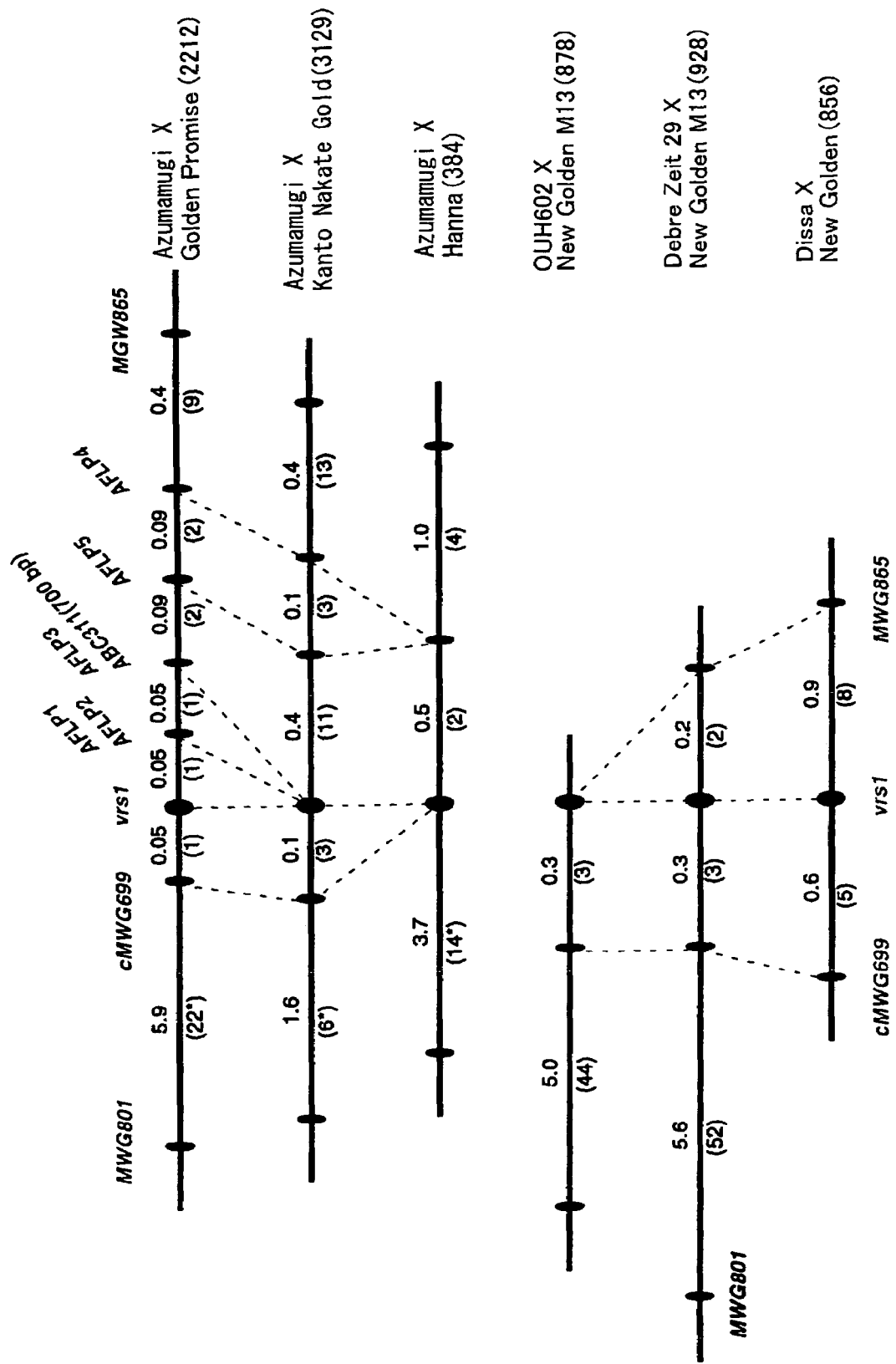
FIG. 2 schematically shows a linkage map for row type based on a total of six populations including the BC6F2 and BC7F1 populations of Azumamugi/Kanto Nakate Gold, and the F2 populations of Azumamugi/Golden Promise and Azumamugi/Hanna. AFLP1 to AFLP5 are abbreviations for the AFLP markers invented in the present invention. Their complete names are listed in Table 2. The other markers were already known.

The linkage between these markers and row type in the above three populations were analyzed, and linkage maps were obtained (FIG. 2). For linkage analysis, information on the row types identified in these lines was integrated with information on known molecular markers for these lines.

TABLE 1

| Population[a] | Generation | Number of segregating plants | Number of chromosomes |
|---|---|---|---|
| Azumamugi × Golden Promise | $F_2$ | 192 and 914 | 2212 |
| Azumamugi × Kanto Nakate Gold[b] | | 1751 | 3129 |
| M4-5 × AZ | $(BC_6F_2)$ | (192 and 908) | (2200) |
| M1-2, M1-7 and M2-1 | $(BC_6F_2)$ | (278) | (556) |
| AZ × M1-7, AZ × M2-1 | $(BC_7F_1)$ | (373) | (373) |
| Azumamugi × Hanna | $F_2$ | 192 | 384 |
| OUH602 × New Golden M13 | $F_2$ | 439 | 878 |
| Debre Zeit 29 × New Golden M13 | $F_2$ | 464 | 928 |
| Dissa × New Golden | $F_2$ | 428 | 856 |

[a]Azumamugi, Dissa, and New Golden M13 are six-rowed, and the other cultivars are two-rowed.
[b]Populations were mapped using plants of near-isogenic lines for convenience in identifying row type genotype. M4-5, M1-2, M1-7, and M2-1 are plants (individuals) of near-isogenic lines generated by crossbreeding Azumamugi and Kanto Nakate Gold, involving repeated backcrossing with Azumamugi (Komatsuda et al. (1995, 1997, 1999)). Two-rowed M4-5 plants are homozygote, and other three types of plants are heterozygote.

These results are also shown in FIG. 2.

Although the above results were obtained using barley as a material, all barley and related *Triticeae* plants, not only barley, may have similar genetic traits, since the genes in barley and related *Triticeae* plants are known to be homologous. In addition, using the methods of the invention, it may be possible to confer FHB resistance to these plants. Recently, it has been discovered that the two-rowed gene is either effective in improving FHB resistance or closely linked with an effective gene. FHB is the most serious disease in barley and related *Triticeae* plants, and development of molecular markers and methods of identifying FHB resistance in earlier generations can be an effective means for introducing FHB resistance. Furthermore, in addition to FHB resistance, other agriculturally important traits, such as various brewing characteristics, flowering time, and plant height, are linked with the two-rowed or six-rowed gene. Thus, the identification methods of the present invention can be applied to the efficient selection of all such traits.

INDUSTRIAL APPLICABILITY

The DNA markers of the invention, which are linked with row type in barley and related *Triticeae* plants, can be used to precisely determine the row type of a test plant using DNA extracted from any organ of the plant, such as a seedling, without observing its spikes. In addition, the DNA markers of the invention can be used to identify FHB resistance in test plants. Because the present invention enables the row type or FHB resistance of plants to be determined from plants in early developmental stages, the efficiency of breeding plants using transfer of a gene for six-rowed spikes, or two-rowed spikes, or Fusarium head blight resistant trait is dramatically improved.

What is claimed is:

1. A method of identifying row type in a barley, comprising screening the plant with at least one molecular marker comprising at least one nucleotide sequence selected from the group consisting of SEQ ID NOs: 1 to 5, that is linked with a gene that controls row type.

2. The method of claim 1, wherein the barley is identified as having two-rowed or six-rowed spikes.

3. The method of claim 1, comprising the following steps (a) to (d):
   (a) preparing a DNA sample from a barley;
   (b) digesting the prepared DNA sample with a restriction enzyme;
   (c) separating the DNA fragments by size; and
   (d) comparing the size of a detected DNA fragment with that of a control.

4. The method of claim 1, comprising the following steps (a) to (d):
   (a) preparing a DNA sample from a barley;
   (b) performing a PCR reaction using primer DNAs, with the prepared DNA sample as a template;
   (c) separating the amplified DNA fragments by size; and
   (d) comparing the size of a detected DNA fragment with that of a control.

5. The method of claim 1, comprising the following steps (a) to (e):
   (a) preparing a DNA sample from a barley;
   (b) digesting the prepared DNA sample with a restriction enzyme;
   (c) performing an AFLP reaction using the digested DNA sample as a template;
   (d) separating the amplified DNA fragments by size; and
   (e) comparing the detected DNA pattern with that of a control.

6. The method of claim 1 further comprising the step of selecting, at an early stage, a plant identified as being two-rowed.

7. The method of claim 1 further comprising the step of selecting, at an early stage, a plant identified as being six-rowed.

8. A method of identifying row type in a barley, comprising screening the plant with at least one molecular marker consisting of at least one nucleotide sequence selected from the group consisting of SEQ ID NOs: 1 to 5, that is linked with a gene that controls row type.

9. The method of claim 8 further comprising the step of selecting, at an early stage, a plant identified as being a two-rowed barley or a six-rowed barley.

* * * * *

SEQUENCE LISTING

```
<160> NUMBER OF SEQ ID NOS: 7

<210> SEQ ID NO 1
<211> LENGTH: 1091
<212> TYPE: DNA
<213> ORGANISM: Hordeum vulgare

<400> SEQUENCE: 1
gactgcgtac caattcgctg aggtacttgc tcgcatagtc atggtgctct ttgcaaactg     60
ccaagaagct ctcgtgcata tagtatgggt ccgcgatgca gatatatttg atgctctccg    120
tcctgatgaa gtagttgaga tacagcgcat acatgcggat gaactggaaa tccaacttgg    180
tcatgtggaa catattgtag atgtagtcaa atcgcaggag gaattgattc gcgggccagg    240
tatcgaagta caccttccca cccggcacct gagccgcgta aagcgggtat cctgaatctt    300
tcacgaccag aaggcttttc tctctggcca gcacatcttc atggagtctc tttagatcat    360
tgttcagtac gtgatctatt gttttggcag gtaggatcgg cttgccggcg acatggaaat    420
gcttcttacc ttcgacgggt attctgtcta ccacccgggg ttccagaggc ggctagctgc    480
ttgaagcatc tatggcgcct ttaagggcct ttcctggcca gtctcttcct ttgcttcttg    540
gtgggtggcg gtagtgaacc caccataccd tccctaacca gcaccccag tgtcatcggg    600 ctagacagtg gacggcctcg gggggttgct ggctagaggt ggcatctcga ggcgtctcct    660
gcgaggatgg cttgaagaga gactttttgc attccacctt aggacgttcc ggctccggaa    720
aatcaggcaa catcaagtca tcgtctccac actcatagcc tatttcttcg gcgtcatgag    780
ccatcaatcc atcataggcg gtattgaaat acttgttcgg gtcctcatca tcatcctcca    840
tgtcattatc aacatttgct tcttcgacag tggggtgaca tgatctggca ctaatggagg    900
ctctccctcg cgttgtacgc taccatcatc tgccacgaca ggtgcaagta atttggtagg    960
tgggatggtg ttcataccdt cttgagaagg tggcgttgga gtgatactgg gctcctcgag   1020
acgaataaga gacttcggcc aaggcaagaa tcagttcttg catgcgccaa tcatcttact   1080
caggactcat c                                                        1091

<210> SEQ ID NO 2
<211> LENGTH: 253
<212> TYPE: DNA
<213> ORGANISM: Hordeum vulgare
```

-continued

<400> SEQUENCE: 2
gactgcgtac caattcgact agccatggtt gtgtatgtat ggcacatggg agtaaaacgt      60
tacaattctt tttgggaacc acacataatg agtatagcat ggaagatact aataacgttt     120
gtcgtaacgt tcacagtaaa gaacaccact caaaattata ttttcaatcc cgctttgaaa     180
acttgagctc taggacttgt gcaaatcaat gcttacctct gcaaagggtc tatctattta     240
ctcaggactc atc                                                       253

<210> SEQ ID NO 3
<211> LENGTH: 260
<212> TYPE: DNA
<213> ORGANISM: Hordeum vulgare

<400> SEQUENCE: 3
gactgcgtac caattctatt agtgacaatc atgctaaaaa tatgcaaaac cctaagcttg      60
gggatgctag ttttgctatg accactacat gattggggta ataatttttc ttattgtgac     120
atccccggat ttaggctaca gtaatcttgg taattgaact acagtaaaca tatgcaaagg     180
atgccacatc atcgtgattc tattattgat ctcgtgatag tcgaaaccga gtcgaaaatc     240
gaagttactc aggactcatc                                                260

<210> SEQ ID NO 4
<211> LENGTH: 158
<212> TYPE: DNA
<213> ORGANISM: Hordeum vulgare

<400> SEQUENCE: 4
gactgcgtac caattcctgt gtgggaaggg gaaaaccaaa gccatcatca tcaccaacgc      60
ttcctccttc gtgggaggat cgatcttcat caacatattc accagcacca tctcatgtcc     120
aaccctagtt catctcgtgt atttactcag gactcatc                            158

<210> SEQ ID NO 5
<211> LENGTH: 514
<212> TYPE: DNA
<213> ORGANISM: Hordeum vulgare

<400> SEQUENCE: 5
gactgcgtac caattcctgc tggagaaaga cgaggtgctg gaggtggttg tcggtgaaga      60
gcacgttcag cttcgtctag acggagtagg caccatcatc atcatgaacc accgtgtcga     120
agagatcctt cgagatggtg tggaagaatg tcacgcccaa gatgcgaccc tatcctcaat     180
ttggcacgaa ggccttgtca tggatagaag cgcatctcgt cgtgtcgcaa gaatggatat     240
cgttacaagt acatgtactg aaaagaagag atatatatag aattggctta cactcgccac     300
aagctacatc agagtcacat cagtacatta cataatcatc aagagcaaga gcagggtccg     360
actacggacg aaaacaaacg ataaaaataa gaacagcgtc cgtccttgct atcccaggct     420
gccggcctgg aacccatcct agatcgatga agaagaagaa gaagaagcaa ctccaaatga     480
acaatcaagg cgctcgcgtt actcaggact catc                                514

<210> SEQ ID NO 6
<211> LENGTH: 20
<212> TYPE: DNA
<213> ORGANISM: Artificial
<220> FEATURE:
<223> OTHER INFORMATION: an artificially synthesized primer sequence

```
<400> SEQUENCE: 6
atggttgtgt atgtatggca                                               20

<210> SEQ ID NO 7
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 7
cagaggtaag cattgatttg                                               20
```